United States Patent [19]

Okazaki et al.

[11] Patent Number: 5,523,467
[45] Date of Patent: Jun. 4, 1996

[54] PROCESS FOR THE PREPARATION OF ALIPHATIC POLYISOCYANATES

[75] Inventors: Koju Okazaki; Yoshinobu Kanemura; Teruyuki Nagata, all of Omuta, Japan

[73] Assignee: Mitsui Toatsu Chemicals, Inc., Tokyo, Japan

[21] Appl. No.: 401,807

[22] Filed: Mar. 10, 1995

[30] Foreign Application Priority Data

Mar. 22, 1994 [JP] Japan .................... 6-050082

[51] Int. Cl.⁶ .................................. C07C 263/00
[52] U.S. Cl. ........................................ 560/347
[58] Field of Search ............................... 560/347

[56] References Cited

U.S. PATENT DOCUMENTS 5,136,086 8/1992 Nagata et al. ................ 560/347

FOREIGN PATENT DOCUMENTS 3-7253   1/1991  Japan .
3-204851 9/1991  Japan .

*Primary Examiner*—José G. Dees
*Assistant Examiner*—Samuel Barts
*Attorney, Agent, or Firm*—Burns, Doane, Swecker & Mathis

[57] ABSTRACT

A process is provided for the preparation of an aliphatic polyisocyanate. Upon reacting an aliphatic polyamine or its hydrochloride or carbonate with phosgene in an inert liquid medium, the reaction is conducted while charging an inert gas into a reaction system.

5 Claims, No Drawings

PROCESS FOR THE PREPARATION OF ALIPHATIC POLYISOCYANATES

BACKGROUND OF THE INVENTION

1. Field of the Invention

This invention relates to a process for preparing an aliphatic polyisocyanate by reacting an aliphatic polyamine or its hydrochloride or carbonate with phosgene.

2. Description of the Related Art

Aliphatic polyisocyanates are extremely useful compounds as raw materials for polyurethane materials, polyurea materials and polyisocyanurate materials in industrial fields such as chemical industry, resin industry and paint industry.

Preparation of an aliphatic polyisocyanate by the phosgene process can be classified roughly into the direct process in which the polyisocyanate is obtained by directly reacting a corresponding polyamine and phosgene and the salt-forming process in which a polyamine salt such as a polyamine hydrochloride or carbonate is first obtained from a corresponding polyamine and hydrochloric acid gas or carbon dioxide gas and the polyamine salt is then reacted with phosgene. Whichever process is employed, a carbamoyl chloride is formed as an intermediate. The carbamoyl chloride is then subjected to dehydrochlorination so that the aliphatic polyisocyanate is prepared.

However, these direct and salt-forming processes are both accompanied by problems. The dehydrochlorination of the carbamoyl chloride into the polyisocyanate takes place at a low reaction velocity and in general, requires a high temperature of at least 120° C., usually 130° C. or higher. When the polyisocyanate so formed is exposed to heat for a long time, the polyisocyanate tends to become tarry, resulting in a reduction in the production yield. Further, hydrochloric acid gas which has been formed as a result of decomposition of the carbamoyl chloride reacts the resultant polyisocyanate, whereby the carbamoyl chloride is formed again. The carbamoyl chloride becomes tarry at a far higher rate than the polyisocyanate, so that the yield is reduced further.

As a solution for the above-described problems, a process has been proposed. According to this process, phosgene is charged at an excess rate to increase the rate of formation of a carbamoyl chloride from a corresponding polyamine and at the same time, to purge hydrochloric acid gas, which remains in a reaction system, out of the reaction system with the excess phosgene, whereby the aliphatic polyisocyanate is prepared with the equilibrium always biased toward the polyisocyanate side. This process can lower the concentration of the carbamoyl chloride during the phosgenation reaction and moreover, can increase the rate of formation of the aliphatic polyisocyanate. This has made it possible to suppress the conversion of the polyisocyanate into tar and hence to obtain the target product at a relatively high yield.

Described specifically, the reaction is conducted generally at a temperature raised to at least 120° C. or 130° C. or higher while charging phosgene at an excess rate.

A further process has also been reported. According to this process, an ester solvent is used to reduce reaction byproducts so that an aliphatic polyisocyanate can be obtained at a high yield (see Japanese Patent Laid-Open Nos. 7253 and 204851/1991).

Even when preparation of an aliphatic polyisocyanate is conducted in accordance with these processes, the conversion of the polyisocyanate into tar cannot be avoided completely, thereby necessitating an additional step for the treatment of the tar. Excess phosgene is entirely wasted as a loss and moreover, requires treatment for making it harmless. These processes therefore cannot still be considered as economically satisfactory processes.

SUMMARY OF THE INVENTION

An object of the present invention is to improve the above-described processes and to provide an economical process for preparing an aliphatic polyisocyanate at a high yield by the phosgene process.

To achieve the above object, the present inventors have proceeded with extensive research. As a result, it has surprisingly been found that charging of an inert gas into a reaction system can bring about improvements such as a reduction in the consumption of phosgene, prevention of the resultant polyisocyanate from becoming tarry and an improvement in the yield, leading to the completion of the present invention.

In one aspect of the present invention, there is thus provided a process for the preparation of an aliphatic polyisocyanate, which comprises, upon reacting an aliphatic polyamine or the hydrochloride or carbonate thereof with phosgene in an inert liquid medium, conducting the reaction while charging an inert gas into a reaction system.

According to the present invention, the target aliphatic polyisocyanate can be efficiently prepared in a high yield with ease while using phosgene in a smaller amount. The process of the present invention therefore has an extremely high value as an industrial preparation process.

DETAILED DESCRIPTION OF THE INVENTION AND PREFERRED EMBODIMENTS

The term "aliphatic polyamine" as used herein includes bifunctional or higher organic amines having an aromatic ring or rings with no amino group directly bonded thereto. For example, the following compounds can be mentioned:

Linear aliphatic polyamines such as pentamethylenediamine, hexamethylenediamine, 2,2,4-trimethylhexamethylenediamine, 2,4,4-trimethylhexamethylenediamine, octamethylenediamine and nonamethylenediamine; cyclic polyamines such as 1,3-bis(aminomethyl)cyclohexane, isophoronediamine, bis(4-aminocyclohexyl)methane, 2,2-bis(4-aminocyclohexyl)propane, m-xylylenediamine, p-xylylenediamine, oxylylenediamine, mixtures of two or more of these xylylenediamine isomers at desired ratios and bis(aminomethyl)norbornene; and amino acid polyamines such as methyl lysinate and aminoethyl lysinate.

In the process of this invention, these aliphatic polyamines are also usable in the form of hydrochlorides or carbonates.

Isocyanates obtained from these aliphatic polyamines or the salts thereof will be called "aliphatic polyisocyanates".

The process of the present invention has a primary feature in that phosgene is reacted with an aliphatic polyamine or a salt thereof mixed in a liquid medium while charging an inert gas, in other words, in that the reaction is conducted while charging the inert gas into a phosgenating reaction system.

The inert gas employed in the present invention is a gas which does not react with materials in the reaction system such as the aliphatic polyisocyanate, phosgene, and hydrochloric acid. Illustrative examples of the inert gas include nitrogen, helium, neon and argon. Whichever gas is employed, excellent advantageous effects can be equally brought about insofar as the gas so used is an inert gas. Nitrogen is however preferred from the standpoint of economy.

No limitation is imposed on the charging rate (i.e., the volume per unit time) of the inert gas into the reaction system because it varies depending on the reaction conditions and apparatus parameters. However, the inert gas may be charged preferably at least 0.2 times or, more preferably, at least 0.5 times as high as the charging rate of phosgene.

In the present invention, the liquid medium is employed to smoothly mix, stir and transfer the raw materials and the reaction mixture so that the aliphatic polyisocyanate can be prepared with ease.

The term "inert liquid medium" as used herein means an organic solvent which is liquid at room temperature and does not react with materials in the reaction system such as the aliphatic polyamine, the aliphatic polyisocyanate, phosgene, and hydrochloric acid. Specific examples of the inert liquid medium include hydrocarbons such as benzene, toluene, mixed xylenes, o-xylene, m-xylene, p-xylene, cumene, 2,2,5-trimethylhexane, decane and ethylcyclohexane; halogenated hydrocarbons such as chlorobenzene, o-dichlorobenzene, m-dichlorobenzene, p-dichlorobenzene, 1,2,3-trichlorobenzene, 1,2,4-trichlorobenzene, 1,3,5-trichlorobenzene and o-dibromobenzene; nitrogen-containing compounds such as nitrobenzene, N,N-dimethylformamide, N,N-dimethylacetamide and N,N-dimethylimidazolidinone; ethers such as dibutyl ether, ethylene glycol dimethyl ether, ethylene glycol diethyl ether, diethylene glycol dimethyl ether, diethylene glycol diethyl ether, anisole, phenetole, methoxytoluene, benzyl ether and diphenyl ether; ketones such as heptanone and diisobutyl ketone; and esters such as amyl formate, n-amyl acetate, isoamyl acetate, methylisoamyl acetate, n-butyl acetate, isobutyl acetate, 2-ethylbutyl acetate, methoxybutyl acetate, ethoxyethyl acetate, methoxyethyl acetate, methoxypropyl acetate, ethyl acetate, hexyl acetate, 2-ethylhexyl acetate, cyclohexyl acetate, methylcyclohexyl acetate, benzyl acetate, phenyl acetate, methyl Carbitol acetate, ethylene glycol diacetate, ethyl propionate, n-butyl propionate, isoamyl propionate, ethyl butyrate, butyl butyrate, isoamyl butyrate, butyl stearate, butyl lactate, amyl lactate, dimethyl phthalate, methyl benzoate and ethyl benzoate. Among these, media which are liquid under normal pressure at an appropriate reaction temperature of 130° C. or higher are preferred in view of the economy of reaction facilities. Of these, esters are particularly preferred because they can act to suppress formation of byproducts called "chlorinated derivatives" in which the isocyanate groups are partly or wholly substituted by chlorine atoms.

These liquid media can be used either singly or in combination. From the standpoint of recovery for reutilization, however, it is preferred to use them singly.

The liquid medium can be used preferably 3–40 times by weight or, more preferably, 4–20 times by weight of the aliphatic polyamine or its salt. Although an amount smaller than 3 times by weight does not necessarily mean that the reaction will be infeasible, it may become difficult to mix and stir the reaction mixture in some instances. Amounts greater than 40 times by weight lead to a deterioration in the volume efficiency, thereby providing no industrial advantage.

The reaction according to the present invention can be conducted in the following manner: (1) an aliphatic polyamine is employed as a raw material and is reacted with phosgene in an inert liquid medium while charging an inert gas; or (2) an aliphatic polyamine is used as a raw material and, subsequent to formation of its salt by its reaction with hydrochloric acid gas or carbon dioxide gas in the inert liquid medium, the salt is reacted with phosgene while charging an inert gas into the mixture of the salt and the medium.

In the above-described manner (1), a two-stage reaction is generally carried out in the inert liquid medium as will be described next. In the first stage, phosgene is charged while maintaining the liquid temperature in a range of 0°–100° C., whereby a reaction on a low temperature side is conducted. Temperatures higher than 100° C. are not preferred as the yield tends to drop. Although the advantageous effects can be brought about fully at any temperatures not higher than 100° C., temperatures lower than 0° C. require an unduly large refrigerating facility so that the process is not very advantageous from the industrial standpoint. Further, this low-temperature-side reaction often gives preferred results when the raw material aliphatic polyamine is also charged concomitantly with phosgene at a rate such that the molar ratio of a functional group (amino groups/$COCl_2$) to the phosgene is between 0.2 and 1.5. In the second stage, the temperature is raised from that in the first stage. While maintaining the liquid temperature at 120°–200° C. or, preferably, at 130°–200° C., charging of the inert gas is initiated in addition to the charging of phosgene and a reaction on a high temperature side is conducted. The reaction velocity tends to become slower at temperatures lower than 120° C. but the yield tends to drop due to formation of tar at temperatures higher than 200° C. Temperatures outside the above range are therefore not preferred. There is no problem or inconvenience whatsoever even if the charging of the inert gas is initiated from the stage of the low-temperature-side reaction.

In the above-described manner (2), the aliphatic polyamine is first reacted with hydrochloric acid gas or carbon dioxide gas in an inert liquid medium to form the salt of the aliphatic polyamine. The reaction temperature during this salt-forming reaction is preferably 0°–60° C. Temperatures lower than 0° C. require an unduly large refrigerating facility as in the manner (1) described above, so that the process is no longer industrially advantageous. Like the low-temperature-side reaction in the above-described manner (1), this salt-forming reaction can bring about preferred results when the raw material aliphatic polyamine is also charged concomitantly with hydrochloric acid gas at a rate such that the molar ratio of a functional group (amino groups/HCl) to the hydrochloric acid gas is between 0.2 and 1.5. Next, after the solid-liquid mixture is heated, phosgene is reacted while charging the inert gas into the solid-liquid mixture. The reaction temperature is preferably 120°–200° C. with 130°–200° C. being more preferred, like the high-temperature-side reaction in the manner (1).

As long as the liquid medium remains in a liquid form, the process of the present invention can be conducted under reduced pressure, under atmospheric pressure or under an elevated pressure higher than atmospheric pressure. In each manner described above, unreacted phosgene and hydrochloric acid are purged with the inert gas, the solvent is eliminated from the reaction mixture, and the residue is then distilled and purified to obtain the aliphatic polyisocyanate.

The present invention will hereinafter be specifically described by examples and comparative examples.

It should however be borne in mind that the present invention is not limited to or by these examples.

EXAMPLE 1

In a 3-l reaction flask equipped with a reflux condenser, a thermometer, a raw material gas inlet tube, an inert gas inlet tube, a liquid raw material dropping device, a liquid medium dripping device, and a stirrer, 1,000 g of trichlorobenzene (boiling point: 210° C.) were charged. Also charged were 136.2 g (1.0 mole) of m-xylylenediamine (hereinafter abbreviated as "m-XDA") in the liquid raw material dropping device and 945 g of trichlorobenzene in the liquid medium dropping device. The total charge of the trichlorobenzene was therefore 14.3 times by weight as much as the charge of the m-XDA.

While stirring the trichlorobenzene cooling in the flask, hydrochloric acid gas was then blown into the liquid at a rate of 36.5 g/hr (1 mole/hr) through the raw material gas inlet tube. Concurrently with the charging of the hydrochloric acid gas, dropping of the m-XDA and trichlorobenzene in the dropping devices was started at a rate of 540.6 g/hr while causing them to merge at a constant weight ratio of 1:6.9. The dropping was completed in 2 hours (the molar ratio of the charged m-XDA to the charged hydrochloric acid gas was 1 in terms of amino groups/HCl). While charging hydrochloric acid gas in the same manner, aging was conducted for 0.5 hour. A series of those salt-forming reaction procedures were conducted at 10° C.

After raising the temperature of the solid-liquid mixture to 160° C., phosgene gas was next blown at a rate of 250 g/hr (2.53 moles/hr) through the raw material gas inlet tube. While concurrently blowing nitrogen gas at a rate of 23 l/hr through the inert gas inlet tube, the internal temperature was raised to 190° C. over 1 hour. While maintaining the temperature, both gases were blown for 3.0 hours to continue the reaction until the reaction mixture became substantially clear.

Unreacted phosgene and the resultant hydrochloric acid gas which remained in the reaction flask were then purged with nitrogen gas. After 0.2 g (as dry) of unreacted m-XDA hydrochloride was filtered off, the liquid medium was eliminated from the filtrate and the residue was distilled under reduced pressure (1–2 mmHg), thereby obtaining 185.3 g of methaxylylene diisocyanate (hereinafter abbreviated as "m-XDi") which contained 2.2 wt.% of methachlorobenzyl isocyanate (hereinafter abbreviated as "m-CBi") (yield of pure m-XDi: 96.34%). The results are also presented in Table 1. Incidentally, the identification of m-CBi and m-XDi was conducted by NMR, MS and IR, and their quantitation was performed by GC. This applies equally to the subsequent examples and comparative examples.

COMPARATIVE EXAMPLE 1

A reaction was conducted in a similar manner to Example 1 except for the omission of nitrogen gas as an inert gas. Unreacted m-XDA hydroxide was filtered off in an amount of 0.1 g (as dry). The other results are presented in Table 1.

TABLE 1

|  | Flow rate of N$_2$ (l/hr) | Flow rate of phosgene (g/hr) | Reaction time (hr) | Total amount stoichiometric amount of phosgene (times in mole relative to stoichiometric amount | m-CBi content (wt. %) | Yield of XDi (%) |
| --- | --- | --- | --- | --- | --- | --- |
| Ex. 1 | 23 | 250 | 4.0 | 5.0 | 2.2 | 96.3 |
| Comp. Ex. 1 | Not charged | 250 | 4.5 | 5.7 | 2.2 | 94.0 |

As is shown in the above table, the charging of inert gas reduces the consumption of phosgene and improves the yield.

EXAMPLE 2

A reactor similar to that employed in Example 1 was used. Charged were 800 g of ethoxypropyl acetate (boiling point: 158° C.) in a 2-l reaction flask, 136.2 g (1.0 mole) of m-XDA in a liquid raw material dropping device and 400 g of ethoxypropyl acetate in a liquid medium dropping device. The total charge of the liquid medium was therefore about 9 times by weight as much as the charge of the m-XDA.

While stirring the liquid cooling in the flask, hydrochloric acid gas was then blown into the liquid at a rate of 36.5 g/hr (1 mole/hr) through the raw material gas inlet tube. Concurrently with the charging of the hydrochloric acid gas, dropping of the m-XDA and ethoxypropyl acetate in the dropping devices was started at a rate of 268.1 g/hr while causing them to merge at a constant weight ratio of 1:2.9. The dropping was completed in 2 hours (the molar ratio of the charged m-XDA to the charged hydrochloric acid gas was 1 in terms of amino groups/HCl). While charging hydrochloric acid gas in the same manner, aging was conducted for 0.5 hour. A series of those salt-forming reaction procedures were conducted at 20°–60° C.

After raising the temperature of the solid-liquid mixture to 135° C., phosgene gas was next blown at a rate of 33 g/hr (0.33 mole/hr) through the raw material gas inlet tube. While concurrently blowing nitrogen gas at a rate of 15 l/hr through the inert gas inlet tube, a reaction was conducted while maintaining the reaction temperature at 135°–140° C. Seventeen hours later, the reaction was completed when the reaction mixture became substantially clear.

Unreacted phosgene and the resultant hydrochloric acid gas which remained in the reaction flask were then purged with nitrogen gas. After 1.2 g (as dry) of unreacted m-XDA hydrochloride were filtered off, the liquid medium was eliminated from the filtrate and the residue was distilled under reduced pressure (1–2 mmHg), thereby obtaining 171.0 g of m-XDi which contained 0.7 wt.% of m-CBi (yield of pure m-XDi: 90.2%).

EXAMPLE 3

The reactor employed in Example 2 was charged as in Example 2 except that the liquid medium was changed from ethoxypropyl acetate to orthodichlorobenzene (hereinafter abbreviated as "ODCB"; boiling point: 180° C.).

While vigorously agitating the liquid cooling in the flask, phosgene gas was then blown into the liquid at a rate of 100 g/hr through the raw material gas inlet tube. Concurrently with the charging of the phosgene gas, dropping of the m-XDA and ODCB in the dropping devices was started at a rate of 178.7 g/hr while causing them to merge at a constant weight ratio of 1:2.9. The dropping was completed in 3 hours (the molar ratio of the charged m-XDA to the charged phosgene was 0.65 in terms of amino groups/$COCl_2$). A series of those reaction procedures were conducted at 0°–30° C.

After gradually raising the temperature of the reaction mixture to 135° C., phosgene gas was next blown at a rate of 20 g/hr (0.2 mole/hr) through the raw material gas inlet tube. While concurrently blowing nitrogen gas at a rate of 23 l/hr through the inert gas inlet tube, a reaction was conducted while maintaining the reaction temperature at 135°–140° C. Eight hours later, the reaction was completed when the reaction mixture became substantially clear.

Unreacted phosgene and the resultant hydrochloric acid gas which remained in the reaction flask were then purged with nitrogen gas. After 0.3 g (as dry) of an insoluble matter was filtered off, the liquid medium was eliminated from the filtrate and the residue was distilled under reduced pressure (1–2 mmHg), thereby obtaining 168.6 g of m-XDi which contained 4.2 wt. % of m-CBi (yield of pure m-XDi: 85.8%).

EXAMPLE 4

Using the reactor employed in Example 2, the procedures of Example 2 were repeated in exactly the same manner up to the salt-forming reaction except that the liquid medium was changed from ethoxypropyl acetate to isoamyl acetate (boiling point: 142° C.) and carbon dioxide gas was substituted for hydrochloric acid gas.

After raising the temperature of the solid-liquid mixture to 100° C., phosgene gas was next blown at a rate of 33 g/hr (0.33 mole/hr) through the raw material gas inlet tube. While concurrently blowing nitrogen gas at a rate of 15 l/hr, which was the same as its blowing rate in Example 2, through the inert gas inlet tube, a reaction was conducted for 8 hours while maintaining the reaction temperature at 100°–105° C. and after raising the temperature to 135° C., the reaction was continued further while maintaining the reaction temperature at 135°–140° C. Ten hours later, the reaction was completed when the reaction mixture became substantially clear.

Next, the reaction mixture was treated as in Example 2. Unreacted m-XDA carbonate was filtered off in an amount of 0.5 g (as dry). The results are presented in Table 2.

COMPARATIVE EXAMPLE 2

Using the reaction employed in Example 4, a reaction and treatment were conducted likewise except that nitrogen gas as an inert gas was not blown in. Unreacted m-XDA carbonate was filtered off in an amount of 0.4 g (as dry). The results are presented in Table 2.

TABLE 2

|  | Flow rate of $N_2$ (l/hr) | Flow rate of phosgene (g/hr) | Reaction time (hr) | Total amount of phosgene (times in mole relative to stoichiometric amount) | m-CBi content (wt. %) | Yield of XDi (%) |
| --- | --- | --- | --- | --- | --- | --- |
| Ex. 4 | 15 | 33 | 18 | 3.0 | 2.8 | 80.4 |
| Comp. Ex. 2 | Not charged | 33 | 18 | 3.0 | 2.8 | 75.8 |

The charging of inert gas also improves the yield in the carbonate process.

EXAMPLES 5–8 & COMPARATIVE EXAMPLE 3

An investigation was conducted about advantageous effects of the inert gas charging. A reaction and treatment were conducted as in Example 2 except that the liquid medium was changed to ethoxyethyl acetate (boiling point: 156° C.) and the charging rate of nitrogen gas was varied. The results are presented in Table 3, in which the term "filter cake" means unreacted m-XDA hydrochloride.

TABLE 3

|  | Flow rate of nitrogen (relative to phosgene) (times by volume) | Reaction time (hr) | Amount of filter cake (g-dry) | m-CBi content (wt. %) | Yield of XDi (%) |
| --- | --- | --- | --- | --- | --- |
| Comp. Ex. 3 | 0 | 17 | 1.9 | 1.2 | 83.5 |
| Example 5 | 0.5 | 17 | 1.7 | 1.2 | 85.1 |
| Example 6 | 1 | 17 | 1.8 | 1.2 | 86.0 |
| Example 7 | 2 | 17 | 1.3 | 0.8 | 89.3 |
| Example 8 | 3 | 17 | 1.2 | 1.0 | 90.6 |

The yield improves substantially in proportion to the amount of inert gas blown in.

EXAMPLES 9–12 & COMPARATIVE EXAMPLES 4–7

About advantageous effects of the inert gas charging, an investigation was conducted by changing the liquid medium. A reaction and treatment were conducted as in Example 2 except that the liquid medium was changed. The results are presented in Table 4.

TABLE 4

|  | Flow rate of nitrogen (relative to phosgene) (times by volume) | Reaction time (hr) | Liquid medium | Amount of filter cake (g-dry) | m-CBi content (wt. %) | Yield of XDi (%) |
|---|---|---|---|---|---|---|
| Example 9 | 2 | 16 | ODCB | 1.9 | 3.4 | 89.4 |
| Comp. Ex. 4 | 0 | 16 | ODCB | 1.2 | 3.5 | 87.7 |
| Example 10 | 1 | 20 | Mixed xylene | 5.3 | 2.5 | 87.9 |
| Comp. Ex. 5 | 0 | 20 | Mixed xylene | 5.5 | 2.6 | 86.5 |
| Example 11 | 3 | 16 | Anisole | 0.9 | 1.7 | 91.4 |
| Comp. Ex. 6 | 0 | 16 | Anisole | 1.0 | 1.7 | 82.5 |
| Example 12 | 2 | 17 | MPA | 1.5 | 1.0 | 90.2 |
| Comp. Ex. 7 | 0 | 17 | MPA | 1.3 | 1.0 | 81.3 |

ODCB: Orthodichlorobenzene (boiling point: 180° C.).
MPA: Methoxypropyl acetate (boiling point: 158° C.).
Mixed xylene (boiling point: 138–144° C.)
Anisole (boiling point: 154° C.)

An improvement in the yield by the inert gas charging is similarly observed irrespective of the kind of liquid medium.

EXAMPLES 13–14 & COMPARATIVE EXAMPLES 8–9

Advantageous effects of the inert gas charging was investigated in accordance with the cold/hot two-stage process. A reaction and treatment were conducted as in Example 3 except that the liquid medium and the charging rates of nitrogen and phosgene on a high temperature side were varied.

The results are presented in Table 5.

EXAMPLES 15–21 & COMPARATIVE EXAMPLES 10–16

Advantageous effects of the inert gas charging were investigated following the salt-forming process of Example 2 except that the raw material aliphatic polyamine was varied. Reaction conditions and the like were set as in Example 2. In each example or comparative example, a polyisocyanate corresponding to the polyamine was obtained. The identification of the reaction product was conducted by NMR, MS and IR, and its quantitation was performed by GC. The reaction was conducted until the reaction mixture became substantially clear. The results are presented in Table 6.

TABLE 5

|  | Nitrogen/ phosgene flow rates (l/hr) | Liquid medium | Reaction time on high temperature side (hr) | Total amount phosgene (times in mole relative to stoichiometric amount) | m-CBi content (wt. %) | Yield of XDi (%) |
|---|---|---|---|---|---|---|
| Comp. Ex. 8 | 0/6.8 | ODCB | 11 | 3.1 | 4.3 | 82.6 |
| Ex. 3 | 23/4.5 | ODCB | 8 | 2.3 | 4.2 | 85.1 |
| Ex. 13 | 23/2.3 | ODCB | 11 | 2.1 | 4.3 | 84.2 |
| Comp. Ex. 9 | 0/6.8 | Amyl acetate | 12 | 3.3 | 1.2 | 89.6 |
| Ex. 14 | 23/6.8 | Amyl acetate | 10 | 3.0 | 1.1 | 91.3 |

ODCB: Orthodichlorobenzene (boiling point: 180° C.)
Amyl acetate (boiling point: 142° C.)

In the direct process in which the amine and phosgene are directly reacted, the inert gas charging also achieves an improvement in the yield and a reduction in the consumption of phosgene.

TABLE 6

|  | Flow rate of nitrogen (relative to phosgene, times by volume) | Reaction time (hr) | Aliphatic polyamine | Amount of filter cake (g-dry) | Content of Cl-derivatives (wt. %) | Yield (%) | Resultant polyisocyanate |
|---|---|---|---|---|---|---|---|
| Example 15 | 2 | 15 | HDA | 0.4 | 0.2 | 94.1 | HDi |
| Comp. Ex. 10 | 0 | 15 | HDA | 0.5 | 0.2 | 90.3 | HDi |
| Example 16 | 2 | 15 | TMDA | 0.4 | 0.2 | 94.9 | TMDi |
| Comp. Ex. 11 | 0 | 15 | TMDA | 0.6 | 0.2 | 90.4 | TMDi |
| Example 17 | 2 | 17 | IDPA | 0.4 | 0.1 | 95.6 | IPDi |
| Comp. Ex. 12 | 0 | 17 | IDPA | 0.6 | 0.1 | 91.7 | IPDi |

TABLE 6-continued

|  | Flow rate of nitrogen (relative to phosgene, times by volume) | Reaction time (hr) | Aliphatic polyamine | Amount of filter cake (g-dry) | Content of Cl-derivatives (wt. %) | Yield (%) | Resultant polyisocyanate |
|---|---|---|---|---|---|---|---|
| Example 18 | 2 | 15 | HMDA | 0.5 | trace | 96.5 | HMDi |
| Comp. Ex. 13 | 0 | 15 | HMDA | 0.6 | trace | 94.1 | HMDi |
| Example 19 | 2 | 15 | IPCA | 0.5 | trace | 97.3 | IPCi |
| Comp. Ex. 14 | 0 | 15 | IPCA | 0.5 | trace | 93.9 | IPCi |
| Example 20 | 2 | 17 | H6XDA | 0.2 | 0.1 | 95.2 | H6XDi |
| Comp. Ex. 15 | 0 | 17 | H6XDA | 0.3 | 0.1 | 90.5 | H6XDi |
| Example 21 | 2 | 17 | NBDA | 1.0 | 0.1 | 94.5 | NBDi |
| Comp. Ex. 16 | 0 | 17 | NBDA | 1.3 | 0.1 | 90.0 | NBDi |

HDA: Hexamethylenediamine
TMDA: Trimethylhexamethylenediamine
IDPA: Isophoronediamine
HMDA: Bis(4-aminocyclohexyl)methane
IPCA: 2,2-Bis(4-aminocyclohexyl)propane
H6XDA: 1,3-Bis(aminomethyl)cyclohexane
NBDA: Bis(aminomethyl)norbornene
HDi: Hexamethylene diisocyanate
TMDi: Trimethylhexamethylene diisocyanate
IPDi: Isopharone diisocyanate
HMDi: Bis(isocyanatocyclohexyl)methane
IPCi: 2.2-Bis(isocyanatocyclohexyl)propane
H6XDi: 1,3-Bis(isocyanatomethyl)cyclohexane
NBDi: Bis(isocyanatomethyl)norbornene XDi, an improvement in the yield by the inert gas charging is also substantiated.

EXAMPLES 22–23 & COMPARATIVE EXAMPLES 17–18

Advantageous effects of the inert gas charging was investigated in accordance with the same cold/hot two-stage process of Example 3 except for the substitution of HMDA for m-XDA. A reaction and treatment were conducted likewise except that the charging rates of nitrogen and phosgene on the high temperature side were changed. The results are presented in Table 7.

EXAMPLE 24 & COMPARATIVE EXAMPLE 19

Advantageous effects of the inert gas charging were investigated. A reaction and treatment were conducted as in Example 2 except that the liquid medium was changed to isoamyl acetate (boiling point: 142° C.), the blowing rate of phosgene was modified to 25 g/hr and the charging rate of nitrogen was altered to 10 l/hr. The results are presented in Table 8.

TABLE 7

|  | Nitrogen/ phosgene flow rates (l/hr) | Aliphatic polyamine | Reaction time on high temperature side (hr) | Total amount phosgene (times in mole relative to stoichiometric amount) | Content of Cl-derivatives (wt. %) | Yield of HMDi (%) |
|---|---|---|---|---|---|---|
| Comp. Ex. 17 | 0/4.5 | HMDA | 10 | 2.5 | 0.2 | 90.0 |
| Comp. Ex. 18* | 0/4.5 | HMDA | 5 | 2.0 | 0.1 | 60.0 |
| Ex. 22 | 23/4.5 | HMDA | 5 | 2.0 | 0.2 | 92.9 |
| Ex. 23 | 23/2.5 | HMDA | 8 | 1.9 | 0.2 | 92.7 |

*Unreacted raw materials remained in large amounts.

When HMDi, an aliphatic polyisocyanate other than XDi, is prepared by the direct process, the inert gas charging also achieves an improvement in the yield and a reduction in the consumption of phosgene.

TABLE 8

|  | Flow rate of $N_2$ (l/hr) | Flow rate of phosgene (g/hr) | Reaction time (hr) | Total amount of phosgene (times in mole relative to stoichiometric amount) | m-CBi content (wt. %) | Yield of XDi (%) |
| --- | --- | --- | --- | --- | --- | --- |
| Ex. 24 | 10 | 25 | 15 | 1.9 | 0.4 | 92.9 |
| Comp. Ex. 19 | Not charged | 25 | 15 | 1.9 | 0.4 | 91.7 |

Advantageous effects of the inert gas charging was observed, leading to an improvement in the yield.

What is claimed is:

1. A process for the preparation of an aliphatic polyisocyanate, which comprises, upon reacting an aliphatic polyamine or the hydrochloride or carbonate thereof with phosgene in an inert liquid medium, conducting the reaction while charging an inert gas into a reaction system.

2. The process according to claim 1, wherein the inert gas is nitrogen.

3. The process according to claim 1, wherein the aliphatic polyamine is selected from the group consisting of xylylenediamine, hexamethylenediamine, trimethylhexamethylenediamine, isophoronediamine, bis(aminocyclohexyl) methane, 2,2-bis(aminocyclohexyl)propane, bis(aminomethyl) cyclohexane and bis(aminomethyl)norbornene.

4. The process according to claim 1, wherein the reaction is conducted in an inert liquid medium having a boiling point of 130° C. or higher.

5. The process according to claim 4, wherein the inert liquid medium is an ester.

* * * * *